United States Patent [19]
Kirk, III et al.

[11] Patent Number: 5,151,089
[45] Date of Patent: Sep. 29, 1992

[54] RETRACTABLE PROTECTIVE NEEDLE SHEATH

[76] Inventors: William D. Kirk, III, St. Mary's Road, Lebanon, Ky. 40033; Anthony A. DeCaro, 574 T. P. Cundiff Rd., Columbia, Ky. 42728; Wayne E. Perry, 233 N. 500 W, Columbus, Ind. 47201

[21] Appl. No.: 524,009

[22] Filed: May 16, 1990

[51] Int. Cl.⁵ .............................................. A61M 5/32
[52] U.S. Cl. .................................... 604/192; 604/263
[58] Field of Search ............... 604/192, 263, 198, 187

[56] References Cited

U.S. PATENT DOCUMENTS

| | | | |
|---|---|---|---|
| 4,820,277 | 4/1989 | Norelli | 604/192 |
| 4,883,469 | 11/1989 | Glazier | 604/192 |
| 4,888,001 | 12/1989 | Schoenberg | 604/192 X |
| 4,976,699 | 12/1990 | Gold | 604/192 |

FOREIGN PATENT DOCUMENTS

| | | | |
|---|---|---|---|
| 2618685 | 2/1989 | France | 604/198 |
| 2620341 | 3/1989 | France | 604/198 |

*Primary Examiner*—John D. Yasko
*Attorney, Agent, or Firm*—Donald L. Cox

[57] ABSTRACT

A protective needle sheath is described herein which prevents accidental skin puncture and contact by the sharpened end and shaft of a hypodermic needle. The protective sheath is pivoted with a support base molded as part of the syringe or needle assembly, or capable of being fitted to a needle assembly. A retractable arm is pivotally secured to the support base by a live hinge. The retractable arm being capable of moving from a position in which the needle is encased in a needle channel in the arm, to a position exposing the needle. The retractable arm is moved by applying force to an arm actuator attached to the arm. The needle is locked within the needle channel by friction lock tabs located in the needle channel. The lock tabs are released by applying force to squeeze tabs attached to the arm.

7 Claims, 5 Drawing Sheets

RETRACTABLE PROTECTIVE NEEDLE SHEATH

BACKGROUND OF THE INVENTION

1. Field of Invention

This invention relates to protective needle sheaths. More particularly, this invention relates to a device that protects persons who give injections from accidental puncture wounds and contact with hypodermic and other needles used to inject and withdraw fluids into and out of human and animal tissue.

2. Prior Art

It has long been recognized that puncture by a contaminated hypodermic needle can pose a serious risk of infection. This risk has taken on fatal proportions since the emergence of the AIDS virus. While accidental puncture is still the primary hazard, exposure of the technician or other person to body fluids and possible contamination has become a cause of concern. Such exposure can occur when a person contacts the hypodermic needle shaft after injection. In response to this risk, various needle protection devices have been proposed These devices are generally of four types.

One type employs an end capping device with an open tunnel that provides a guide for the needle shaft. By means of collapsible pivotal members or a foam rubber or plastic sleeve which may have an internally integrated spring, the end cap is attached to a hub which connects to the needle assembly and syringe usually by a friction fit. When an injection is given the collapsible portion allows the needle to penetrate.

U.S. Pat. No. 4,790,828 discloses an assembly comprised of an elongated conical needle cover that protects the needle assembly prior to use and a capping device attached to a hub by a tethering mechanism. The preferred tethering mechanism consists of two arms with a flexible shoulder joint positioned at the midpoint of each arm. By applying force to the neutrally positioned tethering device the capping device is forced over the distal end of the needle and locked in place by means of an internally positioned flange.

U.S. Pat. No. 4,775,369 discloses a needle protection device comprised of a sheath with an internal spring with one end of the sheath attached to the hub portion of the needle attachment and the other end of the sheath containing a molded tubular guide end member which houses the sharpened end of the needle. The sheath contracts during the injection to allow penetration. As the needle is withdrawn, the sheath expands to its original position.

U.S. Pat. No. 4,735,618 shows a protective device for a hypodermic needle comprised of a cylindrical sleeve friction fitted over the hub of the needle assembly and connected by two pivotally movable arms to a needle guard that has a central channel for passage of the needle during the injection and a needle pocket where the distal tip of the needle is placed after use. When force is applied along the needle shaft towards the sharp end point, the pivotal arms collapse by means of joints located on the ends and in the middle of each arm.

A second type of needle protector employs opposing pivotal arms to enclose the needle before and after an injection is given. U.S. Pat. No. 4,820,277 describes a device which uses two pivotally hinged opposing arms which can be opened and closed by means of a mechanical activator, to enclose the needle assembly. In the open position the opposing arms fold back and attach to the syringe barrel.

U.S. Pat. No. 4,664,259 sets forth a device which uses two antipodal members hinged to a needle assembly that can be opened and closed around a needle before and after an injection. These members are connected by a lever which provides for uniform movement of the opposing members from the open and closed positions. With this device the opposing members are locked at an angle perpendicular to the needle shaft.

The third type of needle protector employs a single arm with a slot that, in the closed position, covers the needle shaft and the sharp needle point. The arm can be pivoted away from the needle assembly by a hinge means. After the injection, the arm can be repositioned to cover the contaminated needle. U.S. Pat. No. 3,658,061 depicts the device described above. Similarly, U.S. Pat. No. 4,872,552 shows a first tubular section that attaches to the base of a needle assembly. A second tubular section is attached to the first by a hinge. This second section can be rotated away from the needle point and shaft. After the injection is completed, the second section is pivoted back over the needle and, by pushing a sliding element at the end of the tube, the cover is secured over the needle.

U.S. Pat. No. 4,838,871 discloses a device in which a needle guard is rotatably mounted to the base of a needle assembly by means of trundle studs which correspond to trundle bases in the movable element. A locking ring keeps the needle shaft and point enclosed within the needle guard. When this ring is rotated, a longitudinal slit is exposed allowing the guard to be pivoted away from the needle assembly before the injection is given.

U.S. Pat. No. 4,664,259 discloses a needle housing which is hinged to the base of the needle assembly so that the needle housing can be moved from its initial closed position covering the needle to an open position of 90° and back to a closed position in which the now contaminated needle is secured within the housing by a parked hook-like protrusion.

A fourth type of needle protector includes a protective cover which is much longer than the needle which is employed. Approximately half of the length of the needle is encased in a plastic sleeve. A plastic tube is fitted over this sleeve. In the open position, the tube is secured to the base of the needle assembly. After use the tube can be biased along the plastic sleeve over the remaining portion of the needle shaft and over the sharpened end of the needle. A flange on the inside of the tube locks into a detente on the plastic sleeve thus preventing the needle from being contacted after use.

Each of these prior art devices has important limitations. Most of these devices still present a risk of accidental puncture when force is extended along the needle shaft perpendicular to the skin surface. Many of these devices leave a significant portion of the needle shaft exposed to contact by the person administering the injection after it has been withdrawn and is consequently contaminated with body fluids. Many of the described needle protection devices limit the length of the needle shaft that is available for penetration into tissue. As a result medication may not be delivered to the proper site or the needle may not be able to penetrate far enough to withdraw sample fluids. Several of these devices provide for locking mechanisms which can be prematurely engaged rendering the needle assembly and perhaps the syringe and its contents useless.

Finally, each of these devices hampers the person giving the injection because of the cumbersome nature of their design.

Therefore, it is an object of this invention to provide a protective needle sheath for use with hypodermic needle assemblies.

It is another object of this invention to provide a protective needle sheath that eliminates the risk of accidental puncture before and after an injection.

It is still a further object of this invention to provide a protective needle sheath that completely encases the contaminated needle shaft to prevent skin contamination by body fluids after the injection.

It is still a further object of this invention to provide a protective needle sheath that keeps the entire length of the needle shaft available for maximum penetration into tissue.

It is still a further object of this invention to provide a protective needle sheath that can be operated with one hand without requiring the technician to place his or her finger near the sharpened needle end.

It is still a further object of this invention to provide a protective needle sheath that will allow the person giving the injection enhanced control over the syringe and needle resulting in a more efficient and accurate injection.

These and other objects and features of the present invention will become apparent to those skilled in the art from a consideration of the following detailed description, drawings and claims.

SUMMARY OF THE INVENTION

In accordance with the present invention, there is provided a protective needle sheath intended to furnish an improved safeguard receptacle for a needle assembly comprised of a friction fit sleeve and hypodermic needle of the type including a hollow shaft portion with a sharpened puncturing end through which fluid is impelled or extracted. The protective sheath is comprised of a support base that is fitted to a needle assembly, said needle assembly being attached to the end of a syringe. A single arm is pivotally secured to the support base and extends from the support base along the needle shaft projecting beyond the puncturing end of the needle. Attached to the arm is an arm actuator. When a force is applied to the arm actuator the arm can be moved from a closed to an open position. The arm is secured to a needle shaft by friction lock tabs that are released by means of squeeze tabs.

In a closed position, the arm encases the needle shaft and its puncturing end. When the needle is to be inserted, pressure is applied to the squeeze tabs. Next, force is applied to the arm actuator causing the arm to pivot away from the puncturing end of the needle. The arm pivots away to allow insertion of the entire needle shaft during the injection without any impedance provided by the protective needle sheath components. In an open position, the arm is fully retracted and the arm and arm actuator act as a stabilizer allowing the person giving the injection greater accuracy during the injection procedure. As or after the needle is withdrawn, a force is applied at the arm actuator toward the puncturing end of the needle. The arm pivots over the needle shaft and puncturing end again encasing the needle shaft and its puncturing end. Pressure is applied to the squeeze tabs and the needle shaft and puncturing end are locked inside the arm. Thus, the needle shaft and puncturing end are prevented from accidentally puncturing or contacting skin or any other type of surface, both before and after the injection.

BRIEF DESCRIPTION OF THE DRAWINGS

The invention will now be described with reference to the accompanying drawings in which.

DETAILED DESCRIPTION OF THE PREFERRED EMBODIMENT

Figure 1:
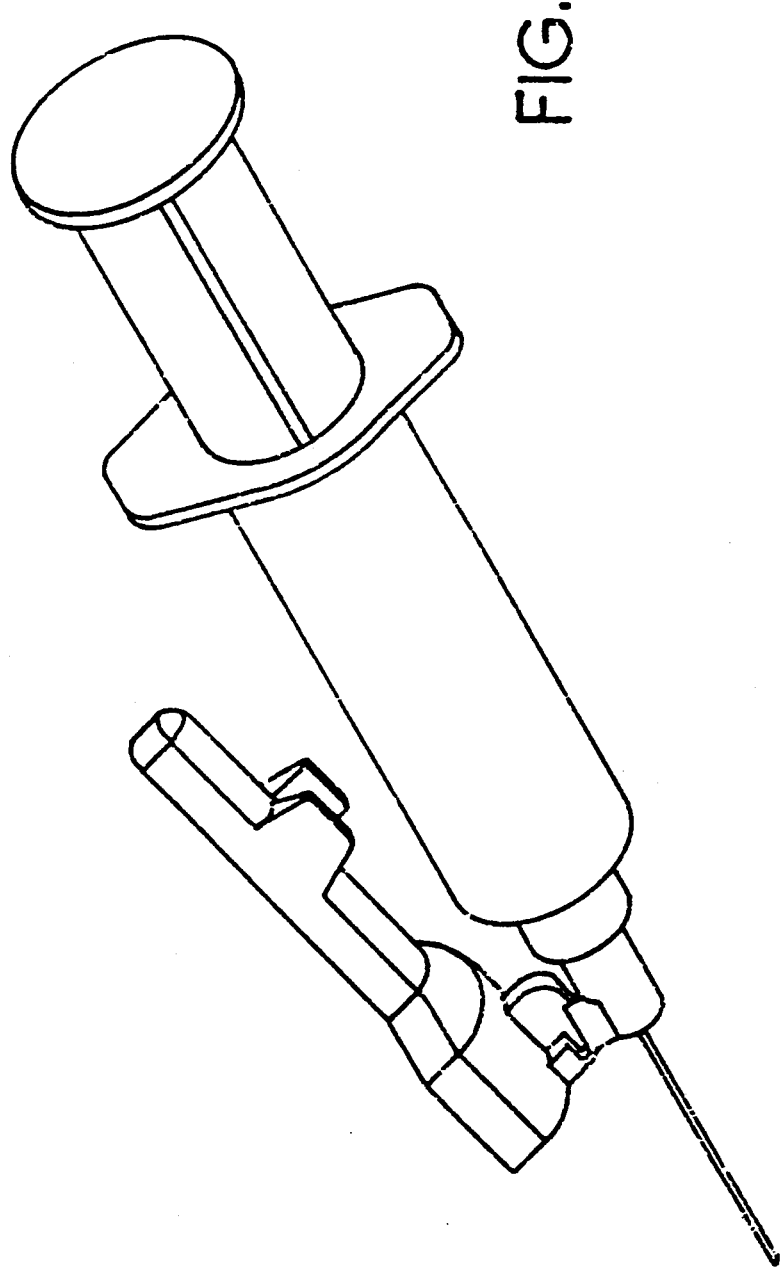
FIG. 1 is a perspective view of the needle protector of the instant invention.
Figure 5:
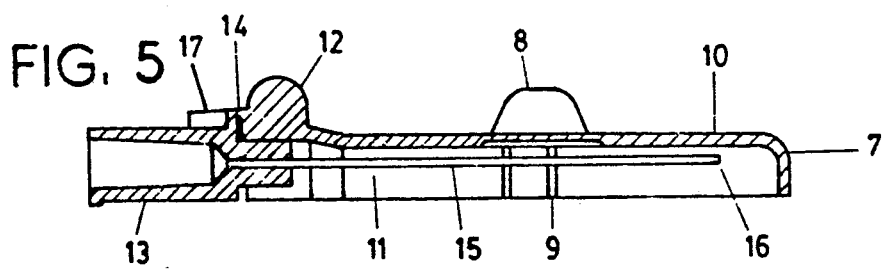
FIG. 5 is a cross-sectional view of the pivotal arm of the needle protective sheath enclosing the needle shaft.
Figure 7:
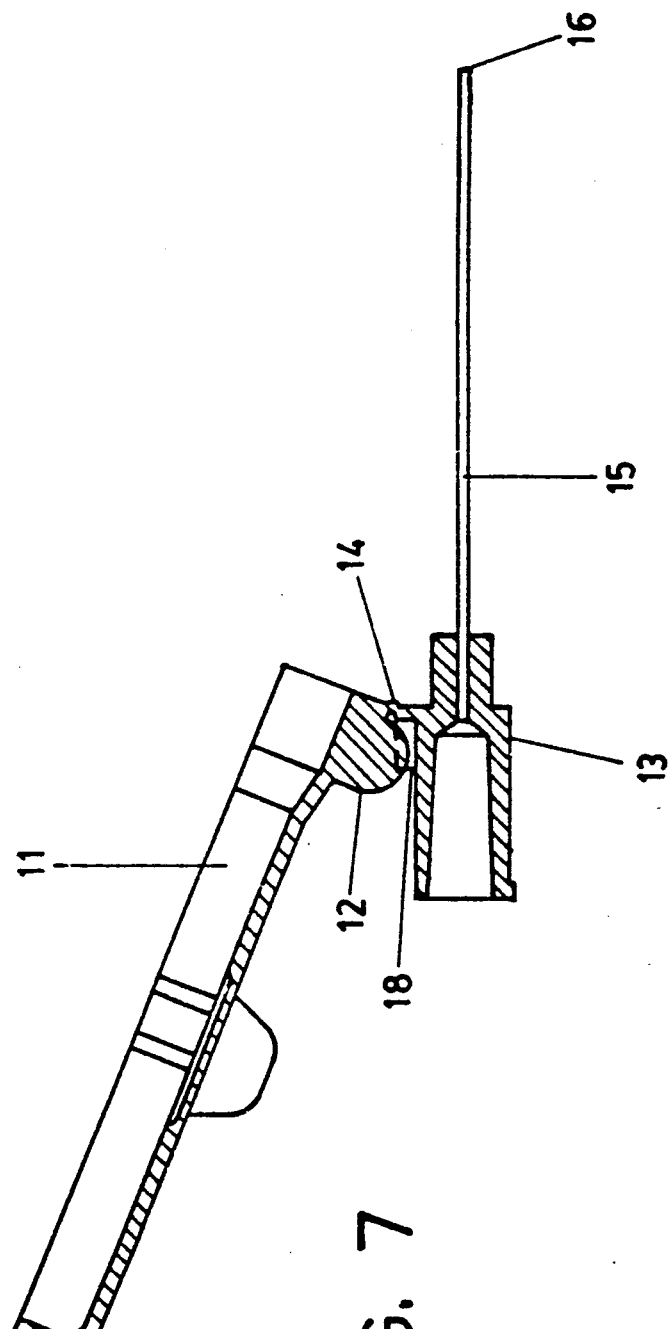
FIG. 7 shows the needle protective in an open position.
Figure 8:
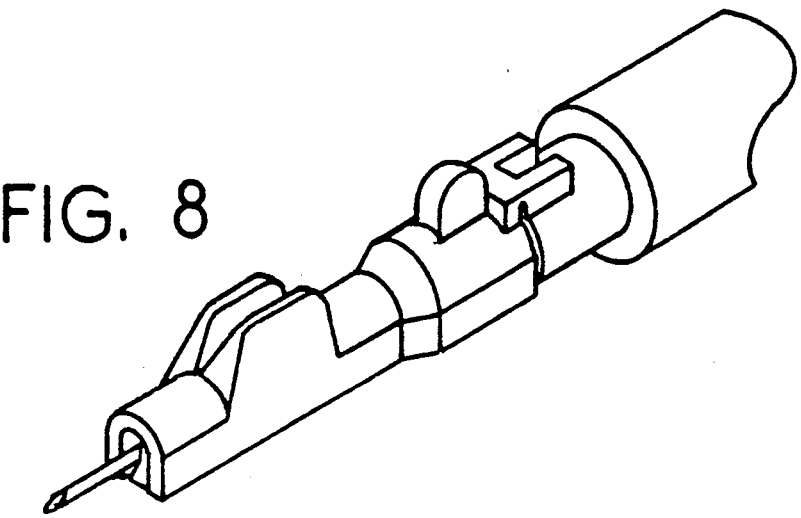
FIGS. 8 and 9 demonstrate the operation of the squeeze tab needle lock.
Figure 9:
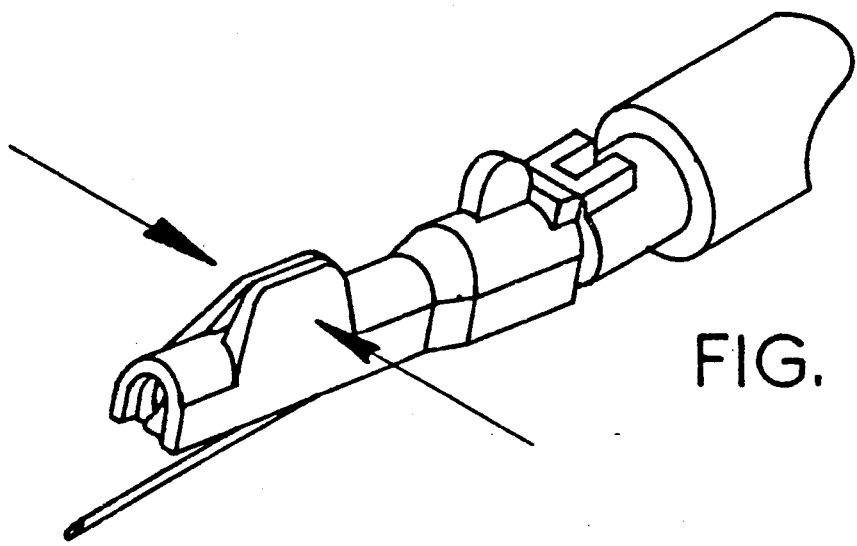

FIG. 1 shows the device as it would be used in an actual practice with the retractable arm secured in the open position by means of engaging the arm actuator (12) in the lock slot (18) as shown more specifically in FIG. 7. The invention as shown in FIG. 5 is a protective needle sheath (7) comprised of a support base (13) and a retractable arm (10) having an arm actuator (12) for applying a bias to the retractable arm (10) which contains a needle channel (11) that allows the retractable arm (10) to completely encase a needle assembly when in a closed position. The retractable arm (10) is locked to the needle assembly by means of friction fit lock tabs (9) which can be disengaged by applying pressure to squeeze tabs (8) as shown in FIGS. 8 and 9.

The support base (13) fits over the male end of a syringe or a hub or a needle assembly, and supports the retractable arm (10) in both open and closed positions as shown in FIG. 5. In a preferred embodiment, the support base can be molded as part of the syringe or a needle assembly hub, or be adapted to fit to existing syringes and needle assemblies by friction or standard leur lock.

Figure 3:
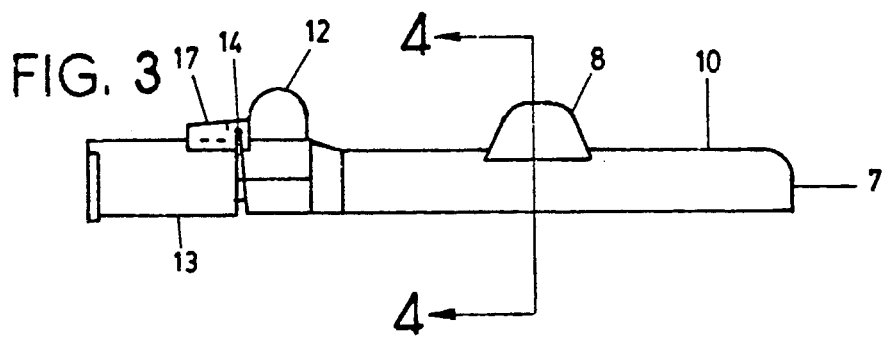
FIG. 3 is a side view of the protective needle sheath in the closed position.

As shown more particularly in FIGS. 3, 5 and 7, the support base (13) is joined to the retractable arm (10) by a pivotal joint (14) located at the point where the needle shaft (15) emerges from the support base (13). The retractable arm (10) pivots in such a manner as to form an enclosure around the needle shaft (15) and the sharpened end point (16) in the closed position as shown in FIG. 5, while allowing the retractable arm (10) to be in the open position without being impeded by the cylindrical portion of the syringe as illustrated in FIG. 7. In the preferred embodiment the retractable arm (10) includes a needle channel (11) running along the length of the retractable arm which accommodates a hypodermic needle as detailed in FIGS. 5 and 6.

Figure 6:
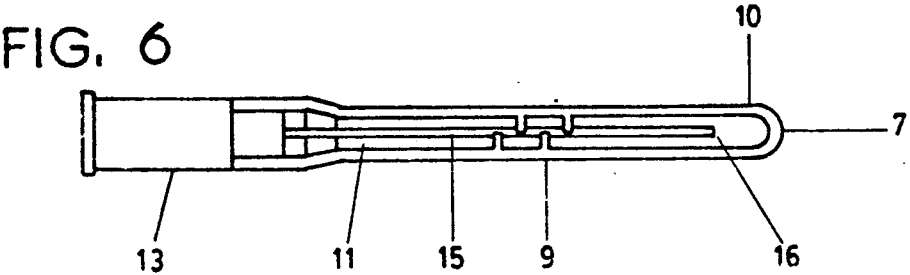
FIG. 6 is a bottom view of the protective needle sheath of the instant invention.

A pivotal joint (14) joins the retractable arm (10) to the support base (13). In the preferred embodiment as shown in FIG. 3, there is one retractable arm (10)

which, in a closed position, protrudes beyond the sharpened needle end (16) and encases the entire length of the needle shaft (15) and sharpened needle end (16). As shown in FIGS. 5 and 6, the retractable arm (10) includes a needle channel (11) on its inside surface of sufficient size to allow the retractable arm (10) to close around the needle assembly.

FIGS. 3 and 5 show an arm actuator (12), attached to the top of the retractable arm (10). By applying force to the arm actuator (12) the retractable arm (10) can be moved from an open to a closed position. In a preferred embodiment the arm actuator (12) forms part of a clasping means (17). This clasping means secures the retractable arm (10) in the open position. In a more preferred embodiment, as shown more particularly in FIG. 7, the retractable arm (10) is locked in the open position by engaging the arm actuator in a lock slot (18).

Figure 2:
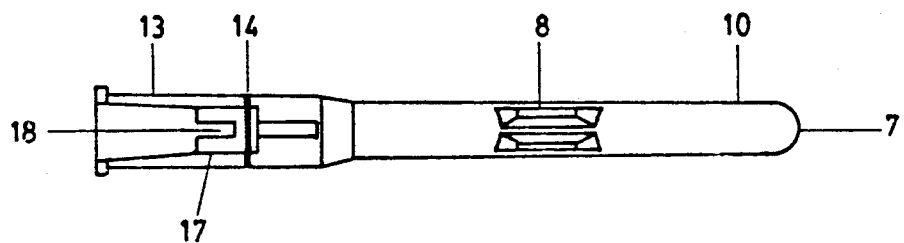
FIG. 2 is a top view of the device in the closed position.
Figure 4:
FIG. 4 is a cross-sectional view of the squeeze tab and friction fit locking tabs.
Figure 10:
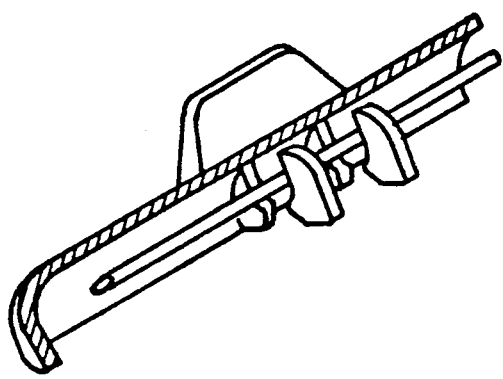
FIG. 10 shows the position of the needle when it is locked inside the needle channel.
Figure 11:
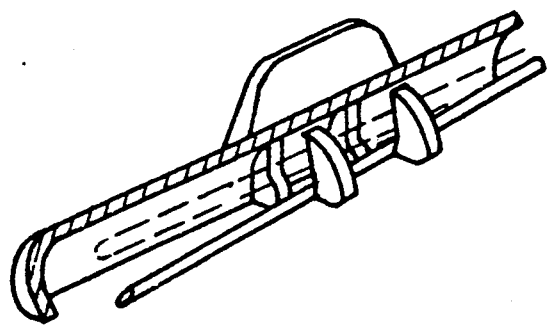
FIG. 11 shows the position of the needle inside the needle channel disengaged from the lock tabs.

As shown in FIGS. 5 and 6, a clasping means is attached to the retractable arm (10) which clasps the retractable arm (10) to the needle shaft (15). In a preferred embodiment squeeze tabs (8) are located on the top of the retractable arm (10) as shown in FIG. 2. FIGS. 4-6 show friction fit locking tabs (9) located on each side of the needle channel (11) below the squeeze tabs (8). As depicted in FIGS. 8 and 9, when pressure is applied to the side of each squeeze tab toward the midline of the retractable arm (10), the friction fit locking tabs (9) open, allowing the retractable arm (10) to be pulled away from the needle shaft. In a more preferred embodiment, as shown more precisely in FIGS. 10 and 11, the friction fit locking tabs (9) are shaped to allow the retractable arm (10) to encase the needle assembly without clasping the friction fit lock tabs (9) to the needle shaft (15). The retractable arm (10) can then be moved to the open position by means of the squeeze tabs (8) or the arm actuator (12), or by applying a force directly to the retractable arm (10) toward the support base (13).

A preferred embodiment contemplates an improvement over existing needle guards in that it provides a protective needle sheath that encases the entire length of the needle shaft (15) and sharp needle end (16). During the injection process this protective needle sheath can be moved from the open position, exposing the needle shaft and sharpened needle end, to the closed position, covering the contaminated needle shaft (15) and sharpened end (16) by applying force to the arm actuator (12) with one finger and thereby eliminating the possibility of a needle puncture wound during this process. Once closed, the retractable arm (10) can be secured over the contaminated needle shaft and needle end preventing any accidental contact between the needle shaft or sharpened end with skin, cloth, or other surface thereby eliminating the risk of exposure and transmission of disease.

In terms of materials, it is intended that the preferred embodiment disclosed herein should be a disposable item. Therefore a material should be employed to permit sterilization of the device without the material changing shape or losing its resiliency. It is envisioned that this device will be formed from a plastic, such as a thermoplastic resin, an example of which is polypropylene.

To use this device, the user applies force to the squeeze tabs (8) to separate the friction fit lock tabs (9). Then the user moves the retractable arm (10) from the closed position to the open position. The retractable arm (10) pivots back by means of the pivotal joint (14) and is secured in an open position that exposes the sharpened needle end (16) and the entire needle shaft (15). To return the retractable arm (10) to the closed position, the user applies force to the arm actuator (12) toward the distal end of the needle shaft (15). By continuing to apply force to the arm actuator (12) toward the distal sharpened end of the needle (16), the retractable arm (10) encases the contaminated needle inside the protective needle sheath, thereby preventing accidental contact with skin and other surfaces The retractable arm (10) is then secured in the closed position by a securing means comprised to the squeeze tabs (8) and the friction fit lock tabs (9).

Many modifications and variations of the present invention are possible with reference to the above description. The invention is not limited to the specific embodiments herein described. Departures may be made from the described device within the scope of the accompanying claims without departing from the principles of the invention and without departing from its chief advantages.

We claim:

1. A protective needle sheath for enclosing a needle including a shaft with a puncturing end comprised of:
   (a) A base means;
   (b) A retractable arm secured to the base by a pivot means wherein said retractable arm extends beyond the puncturing end of the needle shaft and said retractable arm includes a needle channel for encasing the needle;
   (c) An arm actuator secured to the retractable arm to rotate the retractable arm about the pivot means from a closed position wherein the retractable arm encases the needle to an open position wherein the needle is not encased by the retractable arm;
   (d) A clasping means attached to the retractable arm for clasping the retractable arm to the needle shaft when the retractable arm is in the closed position, wherein the clasping means includes friction locking tabs located on each side of the needle channel; and
   (e) Squeeze tabs secured to the retractable arm which when compressed unclasp the friction locking tabs from the needle shaft when the retractable arm is in a closed position.

2. The protective needle sheath of claim 1 wherein a means for securing the retractable arm in the open position to the base is attached to the arm actuator.

3. The protective needle sheath of claim 1 wherein the retractable arm rotates about the pivot means over at least about 120°.

4. The protective needle sheath of claim 1 wherein the base is affixed to a syringe.

5. The protective needle sheath of claim 1 which is formed from a plastic.

6. The protective needle sheath in claim 1 wherein the retractable arm is secured in the open position by a lock slot which interlocks with the arm actuator.

7. The protective needle sheath of claim 1 wherein said friction locking tabs allows the needle shaft to be encased by the retractable arm without engaging the clasping means and locking the needle into the retractable arm.

* * * * *